United States Patent [19]

Handwerker et al.

[11] Patent Number: 5,362,894

[45] Date of Patent: Nov. 8, 1994

[54] PROCESS FOR PRODUCING AN ESTERIFIED ALKOXYLATED POLYOL

[75] Inventors: Beth M. Handwerker, West Chester; Charles F. Cooper, Paoli, both of Pa.; Bernard C. Sekula, High Bridge, N.J.

[73] Assignees: Arco Chemical Technology, L.P.; CPC International, Inc., both of Englewood Cliffs, N.J.

[21] Appl. No.: 151,330

[22] Filed: Nov. 12, 1993

[51] Int. Cl.$^5$ .............. C07C 51/00; C11C 1/00; C11C 3/00

[52] U.S. Cl. .............. 554/169; 554/149; 554/164; 554/167; 554/168; 554/227; 536/119; 252/174.21; 252/312

[58] Field of Search ............ 554/167, 149, 168, 164, 554/169, 227; 252/174.21, 312; 536/119

[56] References Cited

U.S. PATENT DOCUMENTS

| | | | |
|---|---|---|---|
| 3,337,595 | 8/1967 | Lamont | 260/410.6 |
| 4,849,242 | 7/1989 | Kershner | 426/601 |
| 4,861,613 | 8/1989 | White et al. | 426/611 |
| 4,983,329 | 1/1991 | Cooper | 260/410.7 |
| 5,077,073 | 12/1991 | Ennis et al. | 426/531 |
| 5,118,448 | 6/1992 | Cooper | 554/168 |
| 5,135,683 | 8/1992 | Cooper | 554/151 |
| 5,175,323 | 12/1992 | Cooper | 554/164 |
| 5,213,802 | 5/1993 | Masten | 424/439 |

FOREIGN PATENT DOCUMENTS

| | | |
|---|---|---|
| 415636A2 | 3/1991 | European Pat. Off. . |
| 433016A2 | 6/1991 | European Pat. Off. . |
| 481523A1 | 4/1992 | European Pat. Off. . |
| 0481717 | 4/1992 | European Pat. Off. . |
| 1595369 | 4/1970 | Germany . |
| 207070 | 2/1984 | Germany . |

OTHER PUBLICATIONS

Fatty Acids–Part 2–1961 Interscience Publishers, Inc., New York.

George P. Rizzi, Winton Hill Technical Center. E Taylor: Synthesis of Sucrose Polyesters, 1978.

Mieth: G. et al. "Acaloric Compounds with Fat-Like Functional Properties" Die Nahrung, vol. 27, No. 9, pp. 853–876, 1983.

Aust, L. et al. "Orientational Studies on the Metabolism of Various Acaloric Compounds with Fat-Like Properties In The Rat", Die Nahrung, vol. 32, No. 1, pp. 49-57-1988.

Primary Examiner—José G. Dees
Assistant Examiner—Deborah D. Carr
Attorney, Agent, or Firm—Stephen D. Harper

[57] ABSTRACT

A method of obtaining a fatty acid-esterified alkoxylated polyol useful as a reduced calorie fat substitute is provided. The method utilizes a $C_1$–$C_4$ alkyl ester of a $C_8$–$C_{24}$ fatty acid such as methyl stearate or methyl oleate and a short chain acid-esterified alkoxylated polyol such as the acetate of propoxylated glycerin as reactants.

23 Claims, No Drawings

PROCESS FOR PRODUCING AN ESTERIFIED ALKOXYLATED POLYOL

FIELD OF THE INVENTION

This invention relates to methods whereby substances useful as reduced calorie fat substitutes may be conveniently and economically prepared. More specifically, the invention pertains to a synthetic process wherein a $C_1$–$C_4$ alkyl ester of a $C_8$–$C_{24}$ fatty acid is reacted with a short chain acid-esterified alkoxylated polyol to yield a fatty acid-esterified alkoxylated polyol.

BACKGROUND OF THE INVENTION

A wide variety of substances have been proposed for use as fat substitutes in food compositions. The chemical structures of such substances are selected such that they are more resistant to breakdown by the metabolic process of the human digestive system which normally occur upon ingestion of conventional triglyceride lipids. Because of their increased resistance to digestion and absorption, the number of calories per gram available from the fat substitutes is considerably reduced as compared to common vegetable oils, animal fats, and other lipids. The use of such substances thus enables the preparation of reduced calorie food compositions useful in the control of body weight.

U.S. Pat. No. 4,861,613 (incorporated herein by reference in its entirety) describes one class of particularly useful fat substitutes wherein a polyol such as glycerin is alkoxylated with an epoxide such as propylene oxide and then esterified with any of a number of fatty acids or fatty acid derivatives to form an esterified alkoxylated polyol. These substances have the physical and organoleptic properties of conventional triglyceride lipids, yet are significantly lower in available calories than edible oils owing to their pronounced resistance towards absorption and pancreatic lipase enzymatic hydrolysis. The thermal and oxidative stability of the esterified alkoxylated polyols renders them especially suitable for use in the preparation of reduced calorie food compositions requiring exposure to high temperatures such as fried or baked foods.

Various methods of preparing fatty acid-esterified alkoxylated polyols suitable for use as fat substitutes have been proposed, including, for example, the procedures described in U.S. Pat. No. 4,983,329 (direct esterification of propoxylated glycerin using free fatty acids) and U.S. Pat. No. 5,175,323 (transesterification of propoxylated glycerin using alkyl esters of fatty acids). Although such procedures work well, there still exists a need for improved processes wherein manufacturing costs may be substantially reduced or the formation of undesirable impurities or by-products may be minimized. In particular, since polyoxyalkylenes and fatty substances such as triglycerides, fatty acid esters or free fatty acids will undergo thermal and/or oxidative degradation under extreme conditions, it would be highly desirable to develop fatty acidesterified alkoxylated polyol processes which avoid the use of high reaction temperatures for prolonged periods of time.

SUMMARY OF INVENTION

This invention provides a process for the preparation of a fatty acid-esterified alkoxylated polyol, wherein said process comprises reacting a $C_1$–$C_4$ alkyl ester of a $C_8$–$C_{24}$ fatty acid with a short chain acid-esterified alkoxylated polyol in the presence of a basic catalyst in a reaction zone at a temperature effective to simultaneously form the fatty acid-esterified alkoxylated polyol and a $C_1$–$C_4$ alkyl ester of a short chain acid. The latter product is removed from the reaction zone during said reacting.

In a particularly preferred embodiment, the process of this invention comprises reacting a methyl or ethyl ester of a $C_8$–$C_{24}$ fatty acid with an acetic acid-esterified alkoxylated polyol, said acetic acid-esterified alkoxylated polyol being obtainable by alkoxylation of a polyol having from 3 to 8 hydroxyl groups selected from $C_3$–$C_{12}$ aliphatic triols, $C_4$–$C_{12}$ aliphatic tetrols, $C_5$–$C_8$ sugar alcohols, monosaccharides, disaccharides, alkyl glycosides, and glycerol oligomers with an epoxide selected from ethylene oxide, propylene oxide, or 1,2-butene oxide to form an alkoxylated polyol and esterification of the alkoxylated polyol with acetic acid or an equivalent thereof, in the presence of from 0.5 to 2.5 weight percent of a sodium or potassium alkoxide catalyst in a reaction zone at a temperature of from 70° to 160° C. to simultaneously form the fatty acid-esterified alkoxylated polyol and a methyl or ethyl ester of acetic acid, the latter product being continuously removed in vapor form from the reaction zone by distillative means during said reacting.

Additionally, this invention furnishes an integrated process for synthesizing fatty acid esterified alkoxylated polyols from fatty acid triglycerides.

DETAILED DESCRIPTION OF THE INVENTION

The lower alkyl esters of $C_8$–$C_{24}$ fatty acids useful as one of the reactants in the process of the invention described herein are well-known in the art and may be conveniently obtained by alcoholysis of fatty acid triglycerides using a $C_1$–$C_4$ alcohol such as methanol or ethanol or by triglyceride hydrolysis followed by esterification with an alcohol. Triglycerides suitable for such transformations include naturally occurring or synthetically prepared or modified triesters of glycerin wherein all of the long chain acyl groups are attached directly by means of ester linkages to a glyceryl backbone. Illustrative $C_1$–$C_4$ alkyl esters of $C_8$–$C_{24}$ fatty acids include, but are not limited to, methyl, ethyl, n-propyl, isopropyl, n-butyl, isobutyl, sec-butyl and tert-butyl esters of such fatty acids as caproic, pelargonic acid, capric acid, lauric acid, myristic acid, palmitic acid, stearic acid, lignoceric acid, behenic acid, isostearic acid, oleic acid, linoleic acid, palmitoleic acid, linoleic acid, linolenic acid, arachidonic acid, eleostearic acid, eicosenoic acid, elaidic acid, erucic acid, arachidic acid, margadc acid, undecylic acid, pentadecanoic acid-, and the like. Esters of linear, branched, saturated, or unsaturated (mono- or poly-) fatty acids may all be used to advantage. Methods of preparing such esters are described, for example, in Ralston, *Fatty Acids and Their Derivatives*, John Wiley & Sons, pp 498–500 (1948), Markley, "Esters and Esterification", in *Fatty Acids — Their Chemistry, Properties, Production, and Uses,* Markley, ed., Pad 2, Interscience, Chapter IX, pp 867–872 (1961), and Naudet, *Rev. Ferment, Ind. Aliment* 14,268 (1959). Suitable $C_8$–$C_{24}$ fatty acid alkyl esters are also available from commercial sources including, for example, the Humko Chemical Division of the Witco Corporation and the Emery Group of the Henkel Corporation. Mixtures of $C_1$–$C_4$ alkyl esters of $C_8$–$C_{24}$ fatty acids may be utilized; the use of mixtures of alkyl esters of fatty acids obtained by alcoholysis of natural fats and oils such as soybean oil, corn oil, cottonseed oil, olive oil, peanut oil, palm oil, coconut oil, cocoa butter, rapeseed oil (low or high erucic), safflower oil, fish oil, butter, lard, tallow or fully or partially hydrogenated derivatives thereof is especially desirable. A key and unexpected advantage of the process of this invention is that the fatty acid alkyl esters need not be subjected to any special purification prior to use in order to obtain fatty acid-esterified alkoxylated polyol of satisfactory quality. In contrast, it has been reported (U.S. Pat. No. 4,942,228 and European Pat. Pub. No. 424,066) that lower alkyl esters of fatty acids to be used in the esterification of sucrose must be carefully pretreated if a fat substitute having acceptable color, taste, and odor is des i red.

The other reactant employed in the process of this invention is a shod chain acid-esterified alkoxylated polyol. Such substances are obtainable by the esterification of an alkoxylated polyol with a shod chain acid or its equivalent (halide, arthydride, ester). Suitable short chain acids include $C_2$–$C_4$ monocarboxylic acids such as acetic acid, propionic acid, butyric acid, and the like. The alkoxylated polyol may be produced by reaction of a polyol with an epoxide under conditions whereby the epoxide ring-opens and is added onto the hydroxyl groups of the polyol so as to form oxyalkylene segments. Additional epoxide may also react such that the oxyalkylene segments are oligomeric or polymeric in character.

The polyol is preferably a polyhydric aliphatic compound having from 3 to 8 hydroxyl groups such as, for example, $C_3$–$C_{12}$ aliphatic triols (e.g., glycerin, 1,2,4-butanetriol, 2,3,4-pentanetriol, 2-ethyl-2-(hydroxymethyl)- 1,3-propanediol, 1,1,1-tris(hydroxymethyl) ethane, 1,2,6-trihydroxyhexane, 1,2,3-heptanetriol, and the like), $C_4$–$C_{12}$ aliphatic tetrols (e.g., pentaerythritol, erythritol, 2,3,4,5-haxane tetrol), $C_5$–$C_8$ sugar alcohols [including those compounds corresponding to the formula $HOCH_2(CHOH)_nCH_2OH$ wherein n is 3 to 6 such as xylitol, sorbitol, arabitol, mannitol, and the like], monosaccharides (e.g., erythrose, threose, ribose, arabinose, xylose, lyxose, altrose, altrose, glucose, mannose, gulose, idose, galactose, fructose, galactose, and the like), disaccharides (e.g., sucrose, lactose, maltose), and alkyl glycosides (e.g., methyl glycosides, ethyl glycosides, propyl glycosides, and other glycoside compounds wherein the alkyl glycoside is an acetal formed by interaction of a $C_1$–$C_{20}$ alcohol with a carbonyl group of a mono- or disaccharide such as glucose. Oligomers or condensates of the foregoing polyols may also be utilized such as polyglycerol or polypentaerythritol. Most preferably the polyol is glycerin (also known as glycerol).

The oxyalkylene segments in the alkoxylated polyol are preferably derived by ring-opening $C_2$–$C_{10}$ epoxides, especially aliphatic epoxides, such as ethylene oxide, propylene oxide, 1,2-butene oxide, 2,3-butene oxide (cis and/or trans), isobutylene oxide, 1,2-pentene oxide, 1,2-octene oxide, cyclohexene oxide, phenyl glycidyl ether, methyl glycidyl ether, ethyl glycidyl ether, styrene oxide, epichlorohydrin, allyl glycidyl ether, and the like. Due to their low cost, high reactivity, and favorable impact on esterified alkoxylated polyol fat substitute properties, the use of ethylene oxide, propylene oxide, 1,2-butene oxide or mixtures thereof (either in random or block fashion) is especially desirable. Each ring-opened epoxide unit within the oxyalkylene segments has the general skeletal formula

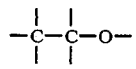

containing two carbon atoms and one oxygen atom. However, the ring-opened epoxide unit may be substituted with one or more alkyl, aryl, aralkyl, or other such substitutent. In a preferred embodiment, the individual ring-opened epoxide units correspond to the structure

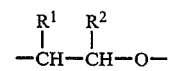

wherein $R^1$ and $R^2$ are the same or different and are hydrogen or a $C_1$–$C_6$ alkyl group such as methyl, ethyl, propyl, isopropyl, butyl, sec-butyl, iso-butyl, tert-butyl, pentyl, hexyl, cyclohexyl, and the like. More preferably, one of $R^1$ or $R^2$ is methyl and the remaining R group is hydrogen. In one desirable embodiment, $R^2$ in the ring-opened epoxide unit adjacent to the acyl group is a $C_1$–$C_6$ alkyl group since a secondary ester linkage resistant to enzymatic hydrolysis is thereby created. In preferred embodiments of the invention, the number of ring-opened epoxide units within each oxyalkylene segment ranges from 1 to 10.

An especially preferred method for obtaining short chain acid-esterified alkoxylated polyols suitable for use in the practice of this invention is to alkoxylate the polyol with the epoxide in the presence of a basic catalyst such as an alkali metal hydroxide or alkoxide to form an alkoxylated polyol. Preferably, from n to 10 n moles of epoxide per mole of polyol is reacted, where n is equal to the number of hydroxyl groups on the polyol. The alkoxylated polyol is then esterified with the short chain acid or equivalent thereof using standard esterification procedures. One such procedure is reaction of the alkoxylated polyol with an acid anhydride such as acetic anhydride or propionic anhydride. Esterification of the available hydroxyl groups of the alkoxylated polyol will occur readily under mild conditions; the use of a catalyst is not necessary. The short chain acid generated as a co-product may be separated or recovered from the short chain acid-esterified alkoxylated polyol and converted back to an anhydride using known methods. The short chain acid-esterified alkoxylated polyol may alternatively be prepared by reacting the short chain acid itself directly with the alkoxylated polyol while removing water so as to drive the esterification to completion.

In a preferred embodiment of this invention, the short chain acid-esterified alkoxylated polyol will correspond to the general structure

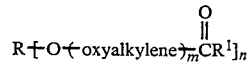

wherein R is an organic moiety derived from the polyol, $R^1$ is $C_1$–$C_3$ alkyl (e.g., methyl, ethyl, n-propyl, isopropyl), n is an integer of from 3 to 8 and m is selected such that the total number of oxyalkylene sequences in the short chain acid-esterified alkoxylated polyol is from n to 10 n. The oxyalkylene sequences are preferably oxyethylene, oxypropylene, oxybutylene, or a combination thereof (random or block). While it is not critical to have complete (100%) esterification of the alkoxylated polyol with the short chain acid, preferably at least 75% of the available hydroxyl groups are esterified.

The short chain acid-esterified alkoxylated polyol in another preferred embodiment of the invention has the general structure

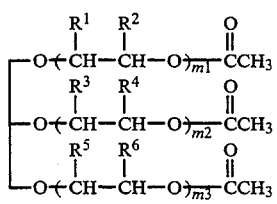

wherein $R^1$ and $R^2$ are different and are hydrogen or methyl, $R^3$ and $R^4$ are different and are hydrogen or methyl, $R^5$ and $R^6$ are different and are hydrogen or methyl, and the total of $m^1 + m^2 + m^3$ is from 3 to 21. Preferably, $R^2$, $R^4$ and $R^6$ are methyl.

While the relative amounts of the $C_1$-$C_4$ alkyl ester of a $C_8$-$C_{24}$ fatty acid and the short chain acid-esterified alkoxylated polyol used in the process of this invention are not critical, generally speaking such amounts are adjusted so as to replace substantially all (i.e. at least 90%, more preferably, at least 95%) of the short chain ester groups on the short chain acid-esterified alkoxylated polyol with long chain fatty acid ester groups. The amount of the $C_1$-$C_4$ alkyl ester of the $C_8$-$C_{24}$ fatty acid is desirably equal to 0.8 n to 1.2 n moles per mole of short chain acid-esterified alkoxylated polyol wherein n preferably is an integer of from 3 to 8 and is equal to the number of short chain acid ester groups on the short chain acid-esterified alkoxylated polyol. More preferably, the amount of the $C_1$-$C_4$ alkyl ester of the $C_8$-$C_{24}$ fatty acid is equal to about n moles per mole of short chain acid-esterified alkoxylated polyol. An important advantage of the process of this invention is that the use of a large excess (i.e., $>1.2$ n moles) of the fatty acid alkyl ester is not necessary in order to achieve a high degree of conversion to the desired fatty acid-esterified alkoxylated polyol.

The catalysts appropriate for use in the instant process will be those substances capable of catalyzing the desired transfer of acyl groups between the different starting components. Such catalysts are typically basic in character and are preferably chosen from among those materials which are alkali metals, alkali metal compounds, alkaline earth metals, alkaline earth metal compounds, or ammonium compounds since such substances exhibit high activity, tend to cause few problems with the formation of undesired by-products or impurities, may be readily removed by conventional techniques after acyl group interchange is accomplished, are relatively non-volatile (thus permitting the selective removal of the $C_1$-$C_4$ alkyl ester of the short chain acid by distillative means from the reaction mixture) and do not generally raise any unusual concerns with respect to toxicity or other harmful effects if trace amounts remain in the esterified alkoxylated polyol product. Illustrative alkali metal, alkaline earth metal, or ammonium compounds which can be utilized include, but are not limited to, ammonium, sodium, lithium, potassium, calcium, barium, or magnesium hydroxides, alkoxides (e.g., methoxides, ethoxides, propoxides, or butoxides, salts of glycerin or other polyols such as diols, triols, tetrols, alkoxylated glycerin, other polyhydric substances), amides, carbonates, bicarbonates, hydrides, oxides, amides, carboxylates (e.g., fatty acid salts), phosphates, borates, sulfates, and the like. Alkali metals such as sodium metal (which may be in the form of a dispersion) or a sodium potassium alloy may be employed. Heterogeneous (insoluble) as well as homogeneous (soluble) catalysts are suitable for use. Basic ion exchange resins such as, for example, the quaternary or tertiary amine-functionalized polystyrenic resins represent one class of heterogeneous catalysts suitable for deployment in the process of this invention. The amount of catalyst is not critical and the optimum concentration can be readily determined by routine experimentation. If the catalyst is an alkali metal or an alkali metal, alkaline earth metal, or ammonium compound, typically the catalyst concentration can suitably be in the range of from 0.01 to 3 weight percent based on the total combined weight of the $C_1$-$C_4$ alkyl ester of the $C_8$-$C_{24}$ fatty acid and the short chain acid esterified alkoxylated polyol. If the basic catalyst is heterogeneous in character, higher catalyst levels (e.g., up to 25 weight percent) may be preferred. If the catalyst is particularly reactive (air or moisture sensitive) or otherwise difficult to handle in pure form, it may be first suspended, dispersed, or dissolved in a suitable carrier or vehicle such as, for example, one or more of the reactants or products (e.g., fatty acid alkyl ester, short chain acid-esterified alkoxylated polyol) prior to use in the process. A catalyst pretreatment of this type will help protect the catalyst from deactivation and degradation and also ensure a uniform distribution of catalyst throughout the reaction mixture.

In an especially preferred embodiment of the invention, the catalyst is a sodium or potassium alkoxide such as sodium methoxide, potassium methoxide, sodium ethoxide, potassium ethoxide, or the like. For reasons that are not well understood, such alkoxides very effectively catalyze the desired reaction between the $C_1$-$C_4$ alkyl ester of the $C_8$-$C_{24}$ fatty acid and the short chain acid-esterified alkoxylated polyol even though such substances fail to adequately catalyze the interesterification of sucrose octaacetate with fatty acid methyl esters (see, for example, Rizzi et al., *J. Am. Oil Chemists Soc.* 55,398(1978)). The preferred concentration of sodium or potassium alkoxide is from 0.5 to 2 weight percent.

The $C_1$-$C_4$ alkyl ester of the $C_8$-$C_{24}$ fatty acid and the short chain acidesterified alkoxylated polyol are contacted in the presence of the basic catalyst for a time and at a temperature effective to accomplish transfer of the $C_8$-$C_{24}$ acyl groups of the former reactant to the latter reactant to generate the desired fatty acid-esterified alkoxylated polyol. At the same time, the short chain acyl groups of the short chain acid esterified alkoxylated polyol are transferred so as to produce a $C_1$-$C_4$ alkyl ester of a short chain acid. For example, where methyl oleate and the triacetate ester of propoxylated glycerin are utilized as the reactants, the expected major products will be methyl acetate and the trioleate ester of propoxylated glycerin. The reactants and catalyst are preferably well agitated or intimately mixed during said contacting so as to minimize reaction times, temperature fluctuation, or product heterogeneity.

The process of this invention is particularly useful for the preparation of the reduced calorie fat substitute described in copending application Ser. No. 07/880,538, filed May 20, 1992, entitled "Esterified Propoxylated Glycerin Fat Substitute Compositions Resistant to Gastrointestinal Side Effects" (incorporated herein by reference in its entirety). The copending application describes a fatty acid-esterified propoxylated glycerin composition useful as a reduced calorie fat substitute resistant to gastrointestinal side effects having an average number of oxypropylene units per equivalent of glycerin of from 3 to 20, a fatty acid acyl group content such that at least 40 mole percent of the fatty acid acyl groups in the composition are derived from a $C_{20}$–$C_{24}$ saturated linear fatty acid, and a solid fat index at 27° C. as measured by dilatometry of at least 30.

If the $C_{20}$–$C_{24}$ saturated linear fatty acid acyl groups in the esterified propoxylated glycerin compositions of copending Ser. No. 07/886,538 are introduced using the free fatty acids, certain processing problems are encountered. In particular, a direct esterification process must generally be run at a relatively high temperature, especially when the only catalytic effect is from the excess fatty acid present. Additionally, a fairly large excess (typically, greater than stoichiometric excess) of fatty acid relative to the initial hydroxyl concentration must be utilized in order to self-catalyze the reaction and to accomplish complete or near-complete esterification of the propoxylated glycerin. As a consequence, the excess fatty acid which remains at the completion of the esterification must be removed prior to formulation of the fat substitute into a food composition, as the excess fatty acid will cause taste, odor, and stability problems. Generally speaking, a convenient way to remove excess fatty acid is by vacuum steam stripping the acids away from an esterified propoxylated glycerin composition. This procedure is quite difficult to accomplish when $C_{20}$–$C_{24}$ saturated linear fatty acids are employed since such acids are relatively high melting (typically, over 74° C.) and consequently readily form troublesome plugs in commercial processing equipment. At times, particularly in vacuum equipment, even steam tracing is not an effective solution due to temperature-lowering effects in the vacuum eductor. As a result, it is often nearly impossible to carry out a large scale non-catalyzed direct esterification of a propoxylated glycerin intermediate with $C_{20}$–$C_{24}$ saturated linear fatty acids without having to frequently shut down to remove plugs of unreacted fatty acid.

We have now found that esterified propoxylated glycerin compositions having a beneficially high level of $C_{18}$–$C_{24}$ saturated linear acyl groups may be conveniently prepared using the process of this invention if at least 40 mole percent of the fatty acid alkyl ester component used as a reactant is a $C_1$–$C_4$ alkyl ester of a $C_{18}$–$C_{24}$ saturated linear fatty acid. For example, methyl or ethyl esters of behenic acid, arachidic acid, or lignoceric acid or mixtures thereof may suitably be utilized. Alkyl esters of this type may be readily obtained by alcoholysis of hydrogenated high erucic rapeseed oil or hydrogenated meadow foam oil.

The reaction conditions are selected such that the desired degree of acyl group interchange takes place within a practically short period of time (typically, from about 1 minute to 12 hours). It has been surprisingly found that the oxyalkylene segments and the fatty acid acyl groups present in certain of the reactants and products are not affected by operation of the process of this invention due to the exceptionally mild conditions employed. The lack of significant degradation of these components ensures that the fatty acid-esterified alkoxylated polyol will require minimal purification to render it suitable for use in food compositions. In particular, the process of this invention yields fat substitutes substantially free of excessive color, off-flavors, and off-odors.

Reaction temperatures of from 0° C. to 200° C. (more preferably, 70° C. to 160° C.) are normally suitable, although higher or lower temperatures could be utilized depending upon the activity of the catalyst. While a solvent could be present in order to facilitate mixing, reduce viscosity, or aid in heat transfer, an important advantage of the process of this invention is that the use of a solvent is not required since the $C_1$–$C_4$ alkyl fatty acid ester, of a $C_8$–$C_{24}$ fatty acid, the short chain acid-esterified alkoxylated polyol, as well as the reaction products are generally in a liquid state at the reaction temperatures normally employed. Moreover, the reactant and products tend to be quite compatible and miscible with each other such that a homogeneous reaction mixture is readily attained even without the use of solvent. The use of an emulsifier or soap is similarly not necessary in order to secure a rapid or uniform reaction, in contrast to the esterification of sucrose with fatty acid alkyl esters. The components of the reaction mixture are preferably stirred, mixed, or agitated in a suitable reaction vessel in order to assure intimate contact on a molecular level and to facilitate the desired acyl group transfer reaction. The process of the invention is advantageously carried out under an inert atmosphere wherein air and oxygen are excluded in order to avoid oxidation of the reaction product.

To accomplish near complete replacement of the short chain ester groups with long chain fatty acid ester groups on the alkoxylated polyol, it is essential to remove the $C_1$–$C_4$ alkyl ester of the short chain acid from the reaction zone or vessel (preferably, shortly after it is formed). This may be readily accomplished by distillative means as the $C_1$–$C_4$ alkyl ester of the shod chain acid will have a relatively low molecular weight and thus be considerably more volatile than the other components present in the reaction mixture. Removal of the $C_1$–$C_4$ alkyl ester may be expedited through the application of vacuum, i.e., by conducting the reaction under subatmospheric (reduced) pressure. The reaction is desirably carried out under a pressure of from about 0.1 to about 200 mm Hg (preferably, from about 1 to 50 mm Hg). Sparging of an inert stripping agent such as nitrogen or a volatile hydrocarbon may also be utilized, either alone or in combination with the application of vacuum. The flow rate of stripping agent may be from 100–2500 liters per hour and per kilogram of reaction mixture (this rate is expressed as liters under the pressure and temperature conditions of the mixture at the moment of stripping). The stripping agent, if any, may be separated from the short chain acid alkyl ester and recycled. The removal conditions are selected such that essentially only the $C_1$–$C_4$ alkyl ester of the short chain acid is taken overhead; the reactants and the fatty acid-esterified alkoxylated polyol product are retained in the reaction zone. To drive the desired reaction to completion, it is desirable to minimize the concentration of the $C_1$–$C_4$ alkyl ester product within the reaction zone. In general, reaction times will be shortened where the $C_1$–$C_4$ alkyl ester product concentration is maintained below 5% by weight (more preferably, below 1% by weight).

The $C_1$–$C_4$ alkyl ester of the short chain acid which is removed from the reaction zone may be condensed and either utilized for other purposes or recycled for use in synthesizing additional quantities of the reactants needed for the process of this invention. For example, the $C_1$–$C_4$ alkyl ester could be hydrolyzed to yield a $C_1$–$C_4$ aliphatic alcohol and a short chain acid. The $C_1$–$C_4$ aliphatic alcohol can be used for the alcoholysis of additional triglyceride, while the short chain acid can be used to esterify additional alkoxylated polyol. Alternatively, the $C_1$–$C_4$ alkyl ester could be subjected to a carbonylation reaction to generate an anhydride of a short chain acid useful for alkoxylated polyol esterification.

If desired, the process of this invention may be carried out in stages wherein the temperature, pressure, catalyst concentration, or rate of $C_1$–$C_4$ alkyl ester of shod chain fatty acid removal is advantageously varied between stages. Multizone continuous interesterification equipment having a serial sequence of separate reaction vessels or a multi-tray column reactor with crossflow or countercurrent stripping equipment could be utilized. The reactants may be combined all at once in the reaction zone or in portions. In one variation, the reaction may be carried out to achieve partial conversion of the reactants prior to removal of any of the $C_1$–$C_4$ alkyl ester of short chain fatty acid from the reaction zone. For example, equilibrium or near-equilibrium between the reactants and products could be attained in a first stage, followed by the initiation of shod chain fatty acid alkyl ester removal in order to increase the yield of fatty acid-esterified alkoxylated polyol.

The process of this invention may be practiced using batch, semicontinuous, or continuous reaction techniques. If the catalyst utilized is heterogeneous in character, a fixed bed, moving bed, or slurry type reactor may advantageously be employed.

When the acyl group transfer reaction has proceeded to the extent desired, the basic catalyst may be removed or deactivated by an appropriate method. For example, if the basic catalyst is an alkali metal, alkali metal compound or alkaline earth compound, the reaction product can be contacted with a particulate absorbent such as magnesium or aluminum silicate at an appropriate temperature (typically, 50° C. to 150° C.) so as to absorb the catalyst onto the absorbent and then filtered. Alternatively, the reaction product can be treated with an acid such as a mineral acid (e.g., hydrochloric acid, sulfuric acid, phosphoric acid) or an organic acid (e.g., acetic acid, oxalic acid, citric acid, tartaric acid) so as to neutralize the basic catalyst. The neutralized catalyst typically forms a precipitate which can be removed by filtration. Treatment with an appropriate ion exchange resin or extraction with water or dilute aqueous acid may also be utilized. If the basic catalyst utilized is heterogeneous in character, it may be removed from the fatty acid-esterified alkoxylated polyol by filtration, decantation, centrifiguration or other means of separating a solid from a liquid phase.

The fatty acid-esterified alkoxylated polyol produced by the process of this invention can be additionally purified or treated if desired using any of the techniques known in the art for refining natural vegetable or animal oils and fats. Such techniques include, but are not limited to, degumming, bleaching, filtration, deodorization, hydrogenation, deacidification (neutralization), steam stripping, dewaxing, fractional crystallization, and the like. Various additives such as stabilizers, anti-oxidants, vitamins and so forth can also be incorporated into the fatty acid-esterified alkoxylated polyol.

Fat substitutes produced in accordance with this invention can replace, in full or in part, conventional edible oils or fats in a cooking oil, frying oil, salad oil, or shortening, for example. Additional uses include combining the fatty acid-esterified alkoxylated polyol with other foodstuff ingredients to form food compositions such as frozen desserts (e.g., sherbert, ice cream, frozen yogurt, milk shakes), baked goods (cakes, doughnuts, muffins, brownies, breads, pies, rolls, pastries, cookies, biscuits, crackers), nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels, fried foods (fried poultry, fritters, fried pies, fried vegetables such as french fried potatoes, fried fish), reformed and comminuted meats (lunch meats, sausage, hot dogs, hamburger), pet foods, meat and egg substitutes or extenders, whipped toppings, gravies and other sauces, frostings, fillings, icings, cocoa butter replacements or blends, candies (especially those normally containing fatty ingredients such as chocolate or peanut butter), soups and dry baking mixes (for muffins, cakes, pancakes, waffles, brownies, and the like). Owing to the fat-like properties and stability of the fatty acid-esterified alkoxylated polyols, minimum reformulation of standard food compositions will generally be required. The viscosity, melting profile, yield point, hardness, thixotropic area, liquid/solid stability, solid fat index, and other physical properties of the fat substitute are preferably selected such that they mimic as closely as possible the analogous properties of the conventional triglyceride being replaced.

Illustrative ingredients which may be used in combination with the fatty acid-esterified alkoxylated polyols obtainable by practice of this invention include carbohydrates (flour, starches, sugars, celluloses, polydextrose or other bulking agents), edible lipids (triglycerides), proteins (from animal or vegetable sources), vitamins, antioxidants, emulsifiers, thickeners, preservatives, colorants, flavors, fragrances, sugar substitutes (saccharin, aspartame, sucralose, cyclamates, and the like), other fat substitutes or fat mimetics (for example, polyol polyesters such as sorbitol polyester and sucrose polyester or caprenin), water, milk, spices, eggs, and the like. Oil-in-water or water-in-oil emulsions can be readily prepared by combining water, the fatty acid-esterified alkoxylated polyol, and (optionally) other ingredients such as emulsifiers. The fat substitutes are particularly suitable for the preparation of food compositions requiring exposure to elevated temperatures. Unlike other proposed fat substitutes such as proteinacious macrocolloids or certain polysaccharide-based substances requiring water to render them fat-like in texture, the fatty acid-esterified alkoxylated polyols produced by this invention are quite stable thermally and do not readily decompose or lose their fat-like properties when heated. The fat substitutes thus may readily be utilized in deep fat frying applications to prepare fried foods such a savory snack, fried chicken, fried fish, french fries, and the like since they will function as effective heat transfer media (that is, they will transmit heat rapidly and uniformly to the food being fried and also provide crisping).

From the foregoing description, one skilled in the art can readily ascertain the essential characteristics of this invention and, without departing from the spirit and scope thereof, can make various changes and modifications of the invention to adapt it to various usages, conditions, and embodiments.

cated until at least 95% conversion of the short Chain acidesterified alkoxylated polyol is achieved.

TABLE I

| EX. # | EPOXIDE | POLYOL | EPOXIDE: POLYOL MOLAR RATIO | SHORT CHAIN ACID | FATTY ACID ALKYL ESTER | BASIC CATALYST | WT. % CATALYST | TEMP. °C. |
|---|---|---|---|---|---|---|---|---|
| 4 | ethylene oxide | trimethylol propane | 10:1 | propionic acid | partially hydrogenated soybean oil fatty acid methyl esters (iodine value = 30) | potassium methoxide | 0.5 | 95 |
| 5 | 1,2-butene oxide | diglycerol | 8:1 | acetic acid | ethyl stearate | sodium potassium alloy | 0.75 | 120 |
| 6 | a | pentaerythritol | 12:1 | butyric acid | fully hydrogenated high erucic rapeseed oil fatty acid methyl esters | potassium hydroxide | 1.0 | 100 |
| 7 | b | sorbitol | 24:1 | acetic acid | corn oil fatty acid propyl esters | sodium hydroxide | 1.5 | 130 |
| 8 | propylene oxide | sucrose | 8:1 | propionic acid | cottonseed oil fatty acid methyl esters | calcium hydroxide | 3.0 | 140 |
| 9 | c | methyl glucoside | 15:1 | acetic acid | beef tallow fatty acid propyl esters | sodium hydride | 1.0 | 125 |
| 10 | propylene oxide | xylitol | 20:1 | isobutyric acid | canola oil fatty acid methyl esters | sodium ethoxide | 1.3 | 100 | a 2:1 mole:mole mixture of ethylene oxide and propylene oxide
b 3:1 mole:mole mixture of propylene oxide and 1,2-butene oxide
c equimolar amounts ethylene oxide and propylene oxide with the ethylene oxide being first reacted with the methyl glucoside The following examples further illustrate the process of this invention, but are not limitative of the invention in any manner whatsoever.

EXAMPLE 1

The triacetate of a propoxylated glycerin containing about 5 moles of propylene oxide per mole of glycerin was reacted with methyl oleate using a 1:3 molar ratio of short chain acid-esterified alkoxylated polyol: $C_1$-$C_4$ alkyl ester of a $C_8$-$C_{24}$ fatty acid in the presence of 1.1 weight percent sodium methoxide. After 2 hours at 110° C. under a partial pressure of 6 mm Hg to remove the methyl acetate coproduct, essentially 100% conversion of the triacetate was observed. The trioleate of the propoxylated glycerin was obtained.

EXAMPLE 2

The procedure of Example I was repeated using 0.5 weight percent sodium metal as catalyst. Heating for 2 hours at 105° C. under a partial pressure of 6 mm Hg resulted in 92% conversion of the triacetate. The trioleate of the propoxylated glycerin was the major product obtained.

COMPARATIVE EXAMPLE 3

To demonstrate the unexpected effectiveness of the process of this invention, the procedure of Example I was repeated using sucrose octaacetate as a substrate instead of propoxylated glycerin triacetate and a 1:8 molar ratio of sucrose octaacetate to methyl oleate. Analysis by thin layer chromatography indicated that little or no esterification of the surcrose octaacetate by the fatty acid methyl ester took place.

EXAMPLES 4–10

To further demonstrate the utility of the process of this invention, the different short chain acid-esterified alkoxylated polyols and $C_1$-$C_4$ alkyl esters of $C_6$-$C_{24}$ fatty acids listed in Table I are reacted using conditions similar to those described in Example 1. In each case, the reaction mixture is heated at the temperature indicated until at least 95% conversion of the short Chain acidesterified alkoxylated polyol is achieved.

We claim:

1. A process for the preparation of a fatty acid-esterified alkoxylated polyol, wherein said process comprises reacting a $C_1$-$C_4$ alkyl ester of a $C_8$-$C_{24}$ fatty acid with a shox chain acid-esterified alkoxylated polyol in the presence of a basic catalyst in a reaction zone at a temperature effective to simultaneously form the fatty acid-esterified alkoxylated polyol and a $C_1$-$C_4$ alkyl ester of a shox chain acid with said $C_1$-$C_4$ alkyl ester of the shox chain acid being removed from the reaction zone during said reacting.

2. The process of claim 1 wherein the $C_1$-$C_4$ alkyl ester of a $C_8$-$C_{24}$ fatty acid is a methyl or ethyl ester.

3. The process of claim 1 wherein the $C_1$-$C_4$ alkyl ester of a $C_8$-$C_{24}$ fatty acid is a $C_1$-$C_4$ alkyl ester of a fatty acid selected from caproic acid, pelargonic acid, caprylic acid, capric acid, lauric acid, myristic acid, palmitic acid, stearic acid, lignoceric acid, behenic acid, isostearic acid, oleic acid, palmitoleic acid, lidoleic acid, linolenic acid, arachidonic acid, eleostearic acid, eicosenoic acid, elaidic acid, erucic acid, arachidic acid, margaric acid, undecylic acid, pentadecanoic acid, and mixtures thereof.

4. The process of claim 1 wherein the shod chain acid-esterified alkoxylated polyol is an acetic acid-esterified alkoxylated polyol.

5. The process of claim 1 wherein the shod chain acid-esterified alkoxylated polyol is a shod chain acid-esterified propoxylated glycerin.

6. The process of claim 1 wherein the short chain acid-esterified alkoxylated polyol is obtained by alkoxylation of a polyol having from 3 to 8 hydroxyl groups selected from $C_3$-$C_{12}$ aliphatic triols, $C_4$-$C_{12}$ aliphatic tetrols, $C_5$-$C_8$ sugar alcohols, monosaccharides, disaccharides, alkyl glycosides, and glycerol oligomers with at least one epoxide selected from ethylene oxide, propylene oxide, and 1,2-butene oxide to form an alkoxylated polyol and esterification of the alkoxylated polyol with a $C_2$-$C_4$ carboxylic acid or equivalent thereof.

7. The process of claim 1 wherein the amount of the $C_1$-$C_4$ alkyl ester of the $C_6$-$C_{24}$ fatty acid is equal to 0.8 n to 1.2 n moles per mole of short chain acid-esterified alkoxylated polyol wherein n is an integer of from 3 to 8 and is equal to the number of short chain acid ester groups on the short chain acid-esterified alkoxylated polyol.

8. The process of claim 1 wherein the basic catalyst is a sodium or potassium alkoxide.

9. The process of claim 1 wherein the temperature is from 70° C. to 160° C.

10. The process of claim 1 wherein the basic catalyst is present at a concentration of from 0.01 to 3 weight percent based on the total weight of $C_1$–$C_4$ alkyl ester of the $C_8$–$C_{24}$ fatty acid and short chain acid-esterified alkoxylated polyol.

11. The process of claim 1 wherein said $C_1$–$C_4$ alkyl ester of the short chain acid is removed from the reaction zone in vapor form by distillative means.

12. A process for the preparation of a fatty acid-esterified alkoxylated polyol, wherein said process comprises reacting a methyl or ethyl ester of a $C_8$–$C_{24}$ fatty acid with an acetic acid-esterified alkoxylated polyol, said acetic acid-esterified alkoxylated polyol being obtained by alkoxylation of a polyol having from 3 to 8 hydroxyl groups selected from $C_3$–$C_{12}$ aliphatic triols, $C_4$–$C_{12}$ aliphatic tetrols, $C_5$–$C_8$ sugar alcohols, monosaccharides, disaccharides, alkyl glycosides and glycerol oligomers with at least one epoxide selected from ethylene oxide, propylene oxide, or 1,2-butene oxide to form an alkoxylated polyol and esterification of the alkoxylated polyol with acetic acid or an equivalent thereof, in the presence of a sodium or potassium alkoxide catalyst in a reaction zone at a temperature of from 70° to 160° C. to simultaneously form the fatty acid-esterified alkoxylated polyol and a methyl or ethyl ester of acetic acid with said methyl or ethyl ester of acetic acid being removed in vapor form from the reaction zone by distillative means during said reacting.

13. The process of claim 12 wherein the polyol is glycerin.

14. The process of claim 12 wherein the epoxide is propylene oxide.

15. The process of claim 12 wherein the sodium or potassium alkoxide catalyst is sodium or potassium methoxide.

16. The process of claim 12 wherein the amount of the methyl or ethyl ester of the $C_8$–$C_{24}$ fatty acid is equal to about n moles per mole of acetic acid-esterified alkoxylated polyol, wherein n is an integer of from 3 to 8 and is equal to the number of short chain acid ester groups on the acetic acid-esterified alkoxylated polyol.

17. The process of claim 12 wherein at least 90% of the acetic acidesterified alkoxylated polyol is reacted.

18. The process of claim 12 wherein the methyl or ethyl ester of the $C_8$–$C_{24}$ fatty acid is obtained by alcoholysis of a triglyceride.

19. The process of claim 18 wherein the triglyceride is obtained from a natural lipid selected from soybean oil, corn oil, cottonseed oil, olive oil, peanut oil, palm oil, palm kernel oil, coconut oil, rapeseed oil, safflower oil, butter, lard, tallow, cocoa butter or fully or partially hydrogenated derivatives thereof.

20. The process of claim 12 wherein the amount of the epoxide is from n to 10 n moles per mole of polyol wherein n is equal to the number of hydroxyl groups on the polyol.

21. The process of claim 12 wherein the concentration of the methyl or ethyl ester of acetic acid is maintained below 5% by weight.

22. The process of claim 12 wherein at least 30 mole percent of the $C_8$–$C_{24}$ fatty acid is a $C_{20}$–$C_{24}$ saturated linear fatty acid.

23. An integrated process for producing a fatty acid-esterified alkoxylated glycerin, wherein said process comprises the steps of
 (a) reacting a fatty acid triglyceride with a $C_1$–$C_4$ alcohol at a temperature effective to simultaneously form glycerin and a $C_1$–$C_4$ alkyl ester of a $C_8$–$C_{24}$ fatty acid;
 (b) separating the $C_1$–$C_4$ alkyl ester of the $C_8$–$C_{24}$ fatty acid and the glycerin;
 (c) reacting the glycerin with a $C_2$–$C_{10}$ epoxide to form an alkoxylated glycerin;
 (d) reacting the alkoxylated glycerin with an anhydride of a shod chain acid to simultaneously form a shod chain acid-esterified alkoxylated polyol and a shod chain acid;
 (e) separating the shod chain acid-esterified alkoxylated polyol from the shod chain acid;
 (f) reacting the $C_1$–$C_4$ alkyl ester of the $C_8$–$C_{24}$ fatty acid with the short chain acid-esterified alkoxylated glycerin in the presence of a basic catalyst in a reaction zone at a temperature effective to simultaneously form the fatty acid-esterified alkoxylated glycerin and a $C_1$–$C_4$ alkyl ester of the shod chain acid, with said $C_1$–$C_4$ alkyl ester of the shod chain acid being removed from the reaction zone during said reacting.

* * * * *

UNITED STATES PATENT AND TRADEMARK OFFICE
CERTIFICATE OF CORRECTION

PATENT NO. : 5,362,894
DATED : November 8, 1994
INVENTOR(S) : Beth M. Handwerker, et. al.

It is certified that error appears in the above-indentified patent and that said Letters Patent is hereby corrected as shown below:

Column 3, lines 17 and 19, delete each occurrence of "shod" insert --short--.
Column 3, line 20, delete "arthydride", insert --anhydride--.
Column 9, line 16, delete "shod", insert --short--.
Column 12, Claim 1, line 32, delete "shox", insert --short--.
Column 12, Claim 1, line 36, delete each occurrence of "shox" insert--short--.
Column 12, Claim 4, line 51, delete "shod", insert --short--.
Column 12, Claim 5, lines 54 and 55, delete each occurrence of "shod", insert short--.
Column 14, Claim 23, lines 36-39 and 46-47, delete each occurrence of "shod", insert --short --.

Signed and Sealed this

Third Day of January, 1995

*Attest:*

BRUCE LEHMAN

*Attesting Officer*  Commissioner of Patents and Trademarks